(12) United States Patent
McManus (10) Patent No.: US 11,751,887 B2
(45) Date of Patent: Sep. 12, 2023

(54) INTEROPERATIVE AIMING ARM

(71) Applicant: DEPUY SYNTHES PRODUCTS, INC., Raynham, MA (US)

(72) Inventor: Joshua McManus, Downingtown, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 701 days.

(21) Appl. No.: 16/719,234

(22) Filed: Dec. 18, 2019

(65) Prior Publication Data
US 2021/0186523 A1  Jun. 24, 2021

(51) Int. Cl.
*A61B 17/16* (2006.01)
*A61B 17/17* (2006.01)
*A61B 17/00* (2006.01)

(52) U.S. Cl.
CPC ........ *A61B 17/164* (2013.01); *A61B 17/1717* (2013.01); *A61B 17/1615* (2013.01); *A61B 2017/00477* (2013.01)

(58) Field of Classification Search
CPC ............................ A61B 17/164; A61B 17/1717
See application file for complete search history.

(56) References Cited

U.S. PATENT DOCUMENTS

| | | | |
|---|---|---|---|
| 8,777,955 B2 | 7/2014 | Park | |
| 9,017,336 B2 | 4/2015 | Park et al. | |
| 9,113,922 B2 | 8/2015 | Clair | |
| 9,808,262 B2 | 11/2017 | Park et al. | |
| 2008/0264109 A1* | 10/2008 | Ritchey | A61B 17/1725 66/88 |
| 2011/0245885 A1* | 10/2011 | Powell | A61B 17/1725 606/86 R |
| 2016/0342766 A1 | 11/2016 | Darwood | |

\* cited by examiner

*Primary Examiner* — Matthew J Lawson
(74) *Attorney, Agent, or Firm* — BakerHostetler (57) ABSTRACT

In one embodiment, a targeting guide is formed by aligning an axis of a cutting instrument with a bone-anchor fixation hole of an intramedullary nail. The cutting instrument is inserted through the bone-anchor fixation hole such that the cutting instrument is in contact with a guide body of a targeting guide, where the targeting guide is supported relative to the intramedullary nail such that the guide body is spaced outwardly from at least a portion of the intramedullary nail along a radial direction. The cutting instrument is then driven through the guide body so as to form an alignment aperture in the targeting guide. The alignment aperture has a central axis that is aligned with the bone-anchor fixation hole.

9 Claims, 6 Drawing Sheets

INTEROPERATIVE AIMING ARM

TECHNICAL FIELD

The present disclosure relates to systems, assemblies, and methods for the insertion and fixation of an intramedullary nail into a medullary canal of a bone.

BACKGROUND

Intramedullary nails have long been used to treat fractures in long bones of the body such as fractures in femurs, tibias, and humeri. To treat such fractures, the intramedullary nail is inserted into a medullary canal of the long bone such that the nail spans across one or more fractures or fragments in the long bone. Bone anchors, such as bone screws, are then inserted through the bone and into the intramedullary nail at opposing sides of a fracture thereby fixing the intramedullary nail to the bone. The intramedullary nail can remain in the medullary canal at least until the fracture is fused.

SUMMARY

In one example, a method comprises aligning an axis of a cutting instrument with a bone-anchor fixation hole of an intramedullary nail, where the bone-anchor fixation hole extends through an outer surface of the intramedullary nail and the outer surface extends between a trailing end of the intramedullary nail and an insertion end of the intramedullary nail. The method further comprises inserting the cutting instrument through the bone-anchor fixation hole such that the cutting instrument is in contact with a guide body of a targeting guide, where the targeting guide is supported relative to the intramedullary nail such that the guide body is spaced outwardly from the outer surface of the intramedullary nail along a radial direction. The method yet further comprises driving the cutting instrument through the guide body so as to form an alignment aperture in the targeting guide, the alignment aperture having a central axis that is aligned with the bone-anchor fixation hole.

In another example embodiment, an intramedullary nail insertion system comprises a targeting guide and a spacer. The targeting guide has a guide body that has at least one solid portion. The spacer is configured to couple the targeting guide to an intramedullary nail that defines a bone-anchor fixation hole that extends along a central axis. The spacer and targeting guide are configured such that, when the spacer couples the targeting guide to the intramedullary nail, the guide body of the targeting guide is spaced radially outward from the intramedullary nail and a surface of the at least one solid portion is intersected by the central axis of the bone-anchor fixation hole of the intramedullary nail.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

DETAILED DESCRIPTION OF ILLUSTRATIVE EMBODIMENTS

Commonly, an intramedullary nail is implanted by driving the nail into a medullary canal of a long bone such as a tibia, fibula, humerus, or femur. To secure the intramedullary nail to the bone, the intramedullary nail can define at least one bone-anchor fixation hole that extends at least partially through the intramedullary nail. For example, the intramedullary nail can include at least one trailing bone-anchor fixation hole at a trailing portion of the intramedullary nail and at least one leading bone-anchor fixation hole at a leading portion of the intramedullary nail. The intramedullary nail can be secured to the bone by (1) drilling, for each bone-anchor fixation hole, a hole in the bone that aligns with the bone-anchor fixation hole, and (2) inserting, for each bone-anchor fixation hole, a bone anchor through the bone and into the bone-anchor fixation hole such that the bone anchor engages the bone on at least one side, such as opposed sides, of the intramedullary nail.

When the intramedullary nail is implanted in the bone, the bone obstructs the surgeon's view of the trailing and leading bone-anchor fixation holes of the intramedullary nail. Therefore, a targeting system or systems can be employed to determine the location of each bone-anchor fixation hole, and/or align a cutting instrument such as a drill bit with each bone-anchor fixation hole. Once the location of a bone-anchor fixation hole is determined and/or the cutting instrument is aligned with the bone-anchor fixation hole, a hole can be drilled into the bone to the bone-anchor fixation hole. A bone anchor can subsequently be inserted through the bone and into the bone-anchor fixation hole.

One method of targeting the at least one bone-anchor fixation hole includes using fluoroscopy to obtain moving X-ray images of the position of the drill bit relative to the bone-anchor fixation hole in real-time. However, the use of fluoroscopy can over expose the patient, and particularly the surgeon who performs numerous such procedures, to harmful X-rays. As an alternative to fluoroscopy, a guide can be affixed to the intramedullary nail, and the guide can be used to target at least one of the bone-anchor fixation holes with a cutting instrument such as a drill bit. Generally, the guide can include an alignment aperture that aligns with at least one bone-anchor fixation hole when the guide is affixed to the intramedullary nail. The cutting instrument can then be guided into the alignment aperture and through the bone to the bone-anchor fixation hole.

The guides and intermedullary nails are manufactured such that the alignment apertures of the guides are aligned with the respective bone-anchor fixation holes of the intramedullary nails. To ensure that the alignment apertures of the guides and bone-anchor fixation holes of the nails are properly aligned, tolerances between the guides and the intramedullary nails are tightly controlled during manufacturing. Moreover, the guides are commonly made from a material, such as carbon fiber, that is radiolucent and strong enough to ensure that the guides stay calibrated to the intramedullary nails. As a result, the guides can be relatively expensive, making them too costly for some areas of the world.

As an alternative to forming guide the guides with high cost materials and exacting tolerances, each guide can be custom constructed for a particular intramedullary nail as will be discussed herein. As a result, manufacturing tolerances between the guides and intramedullary nails need not be as tightly controlled, thereby reducing manufacturing costs. In addition, or alternatively, the guides can be constructed from a low-cost material, such as a thermoplastic, thereby reducing costs of the guides and allowing the guides to be discarded after a single use with a single intramedullary nail.

To custom construct a guide to a particular intramedullary nail, the intramedullary nail can be used as a guide to form at least one alignment aperture in the guide. For example, a cutting instrument, such as a drill bit or reamer, can be guided through the at least one bone-anchor fixation hole of the intramedullary nail and into the guide so as to cut the at least one alignment aperture into the guide. The alignment apertures of the guide can be custom formed after delivery to a medical facility, such as on a back table of an operating facility. As a result, tolerances between the guide and intramedullary nail need not be precisely controlled during transport of the guide. Alternatively, the alignment apertures of the guide can be custom formed prior to delivery, such as at a manufacturing or other facility, in which case, care should be taken during transport to ensure that the guide and/or intramedullary nail are not damaged to deformed in such a manner that causes tolerances between the guide and intramedullary nail to be lost.

Figure 1:
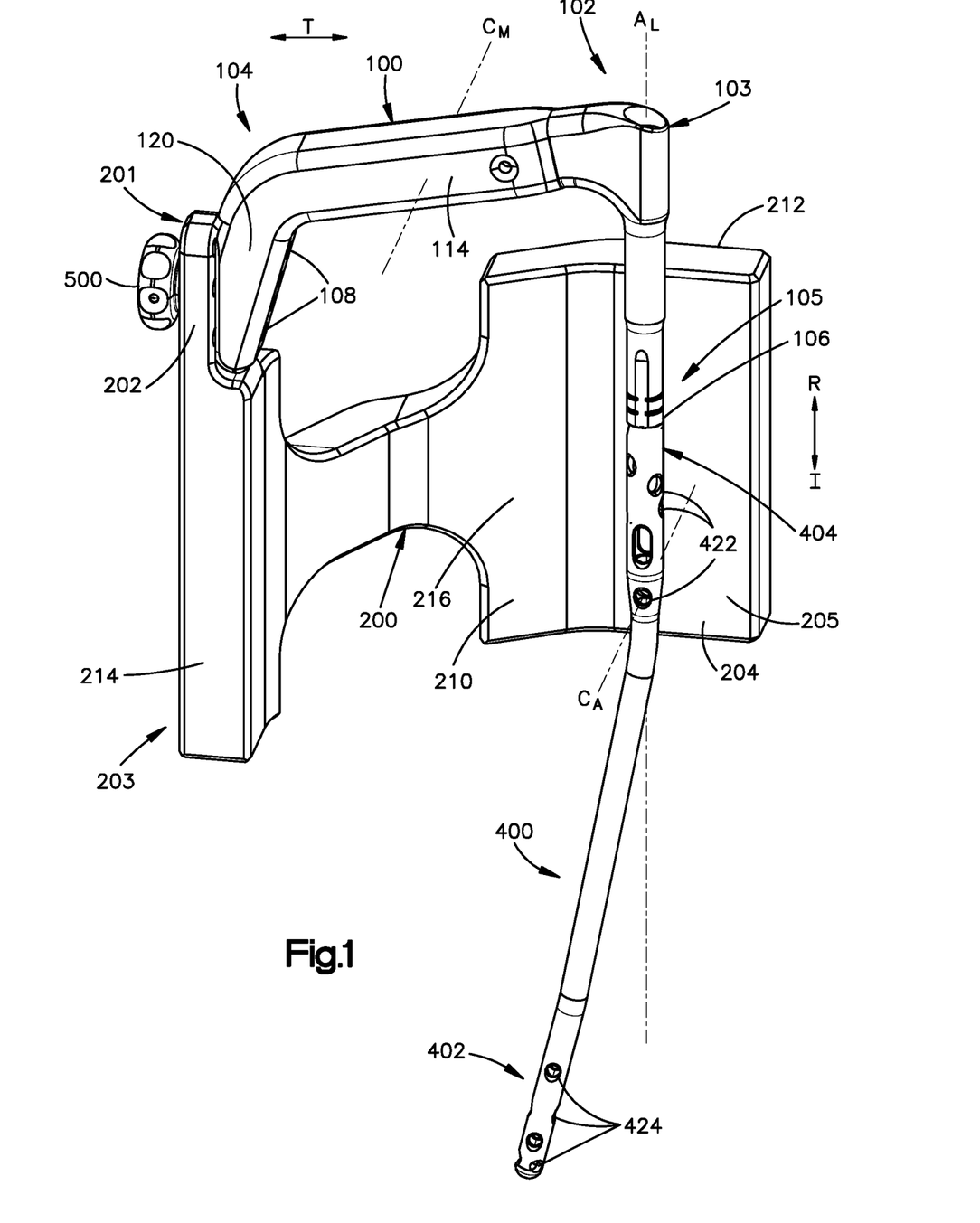
FIG. 1 shows a perspective view of an intramedullary nail insertion system according to one embodiment.
Figure 2:
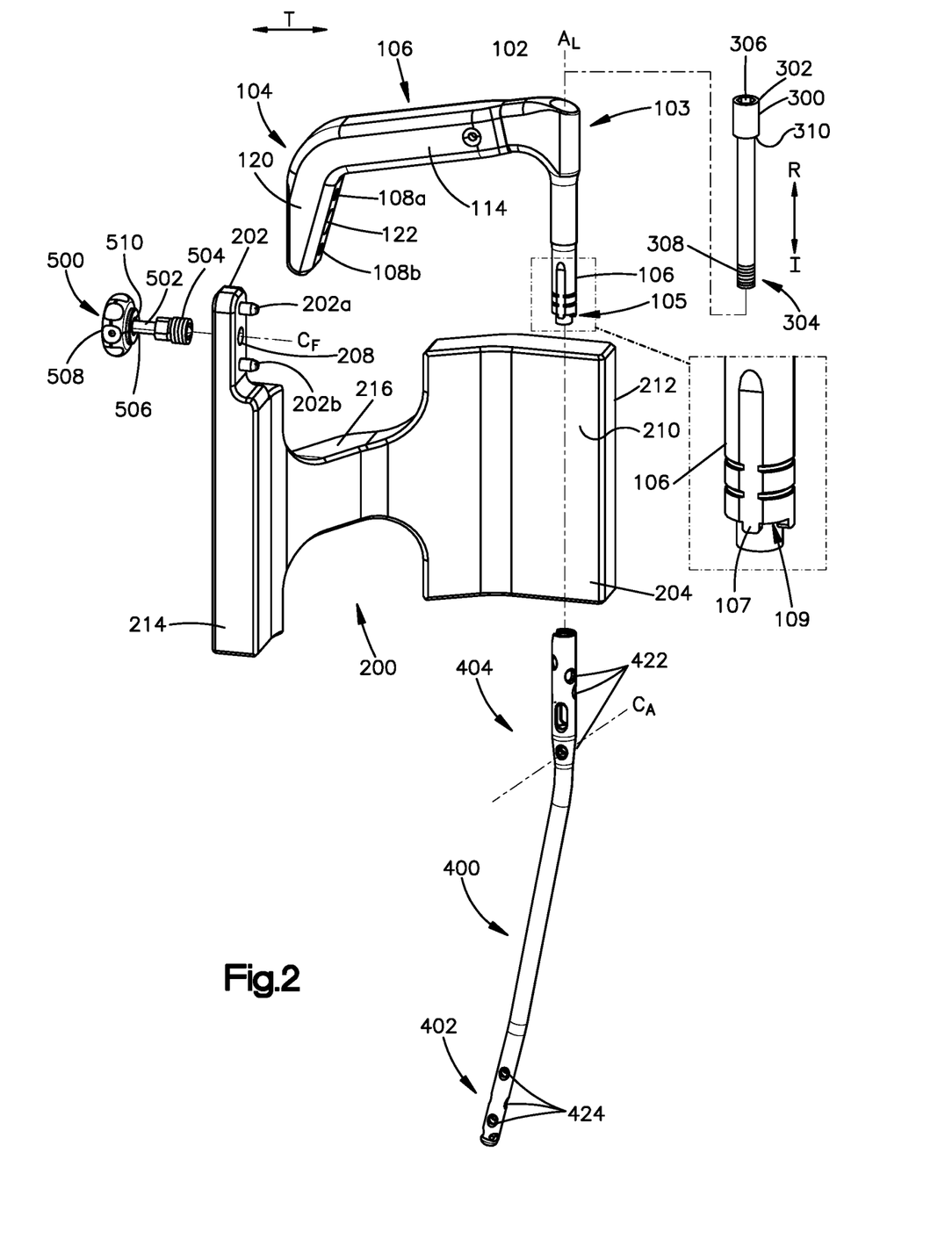
FIG. 2 shows an exploded perspective view of the intramedullary nail insertion system of FIG. 1.

Referring to FIGS. 1 and 2, an intramedullary nail insertion system is shown according to one embodiment. The system comprises a targeting guide 200 and a spacer 100. The spacer can be, for example, an insertion handle that can be used to insert an intramedullary nail 400 into the bone, although embodiments of the disclosure are not so limited. In some embodiments, the system can additionally comprise the intramedullary nail 400. It will be understood, however, that the targeting guide 200, the spacer 100, and the intramedullary nail 400 can be distributed separately from one another or can be distributed in groups of two or more of the targeting guide 200, the spacer 100, and the intramedullary nail 400. Therefore, embodiments of the present disclosure can include as few as one of the targeting guide 200, the spacer 100, and the intramedullary nail 400, or more than one, up to all, of the targeting guide 200, the spacer 100, and the intramedullary nail 400.

Figure 5:
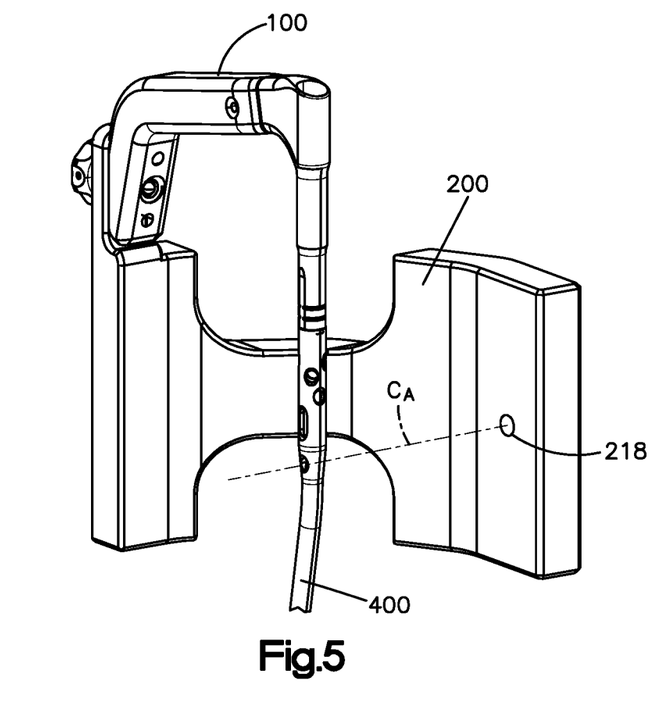
FIG. 5 shows a perspective view of the intramedullary nail insertion system of FIG. 1 with an alignment aperture formed in the targeting guide.

In general, the targeting guide 200 has a guide body 204 that has at least one solid portion 205. The spacer 100 is configured to couple the targeting guide 200 to the intramedullary nail 400 such that a surface of the at least one solid portion 205 is spaced radially outward from the intramedullary nail 400 and is intersected by a central axis $C_A$ of at least one bone-anchor fixation hole 422 of the intramedullary nail 400. The targeting guide 200, and in particular, at least one alignment aperture (e.g., 218 in FIG. 5) of the targeting guide 200, can be custom formed for the particular intramedullary nail 400 with which the targeting guide 200 is to be used. Thus, the targeting guide 200 can have a pre-customized configuration as shown in FIGS. 1-3, wherein at least one alignment aperture (e.g., 218) is not formed in the targeting guide 200, and a customized configuration as shown in FIG. 5, wherein at least one alignment aperture (e.g., 218) is formed in the targeting guide 200.

Figure 4:
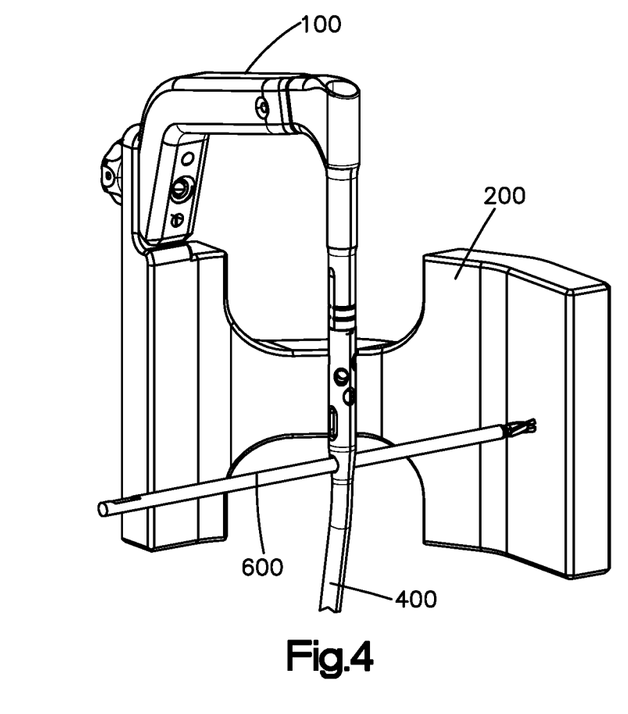
FIG. 4 shows a perspective view of the intramedullary nail insertion system of FIG. 1 with a cutting instrument extending into the targeting guide.

The targeting guide 200 may be customized by aligning an axis of a cutting instrument, such as a drill bit or reamer (e.g., 600 in FIG. 4), with a bone-anchor fixation hole 422 of the intramedullary nail 400. The cutting instrument may then be inserted through the bone-anchor fixation hole 422 such that the cutting instrument is in contact with a surface of the at least one solid portion 205 of the targeting guide 200. In so doing, the cutting instrument may be inserted on a side of the intramedullary nail 400 that is opposite the surface of the at least one solid portion 205 of the targeting guide 200, and directed through the intramedullary nail 400 to the surface of the at least one solid portion 205 of the targeting guide 200. The cutting instrument (e.g., 600 in FIG. 4) may then be driven through the guide body 204 at the surface of the at least one solid portion 205 so as to form an alignment aperture 218 (labeled in FIG. 5) in the targeting guide 200, the alignment aperture 218 having a central axis $C_A$ that is aligned with the bone fixation hole 422 of the intramedullary nail 400. Thus, the intramedullary nail 400, and in particular, the bone-anchor fixation hole 422 can be used as a guide to form at least one alignment aperture 218 in the targeting guide 200 such that each of the at least one alignment aperture 218 aligns with a corresponding bone-anchor fixation hole 422.

In some embodiments, a plurality of bone-anchor fixation holes 422 can be used as guides to form a plurality of alignment apertures 218 in the targeting guide 200 such that each alignment aperture 218 aligns with a corresponding bone-anchor fixation hole 422. Thus, the aforementioned process can be repeated by inserting the cutting instrument through one or more other bone-anchor fixation holes 422 to form one or more other alignment apertures 218, each corresponding to one of the other bone-anchor fixation holes 422. The intramedullary nail 400 can be subsequently implanted into the bone, and the at least one alignment aperture of the targeting guide 200 can be used to target the at least one bone-anchor fixation hole 422 with a cutting instrument, such as a drill bit or reamer. The cutting instrument can be guided into the at least one alignment aperture and through the bone to the at least one bone-anchor fixation hole 422.

Figure 3:
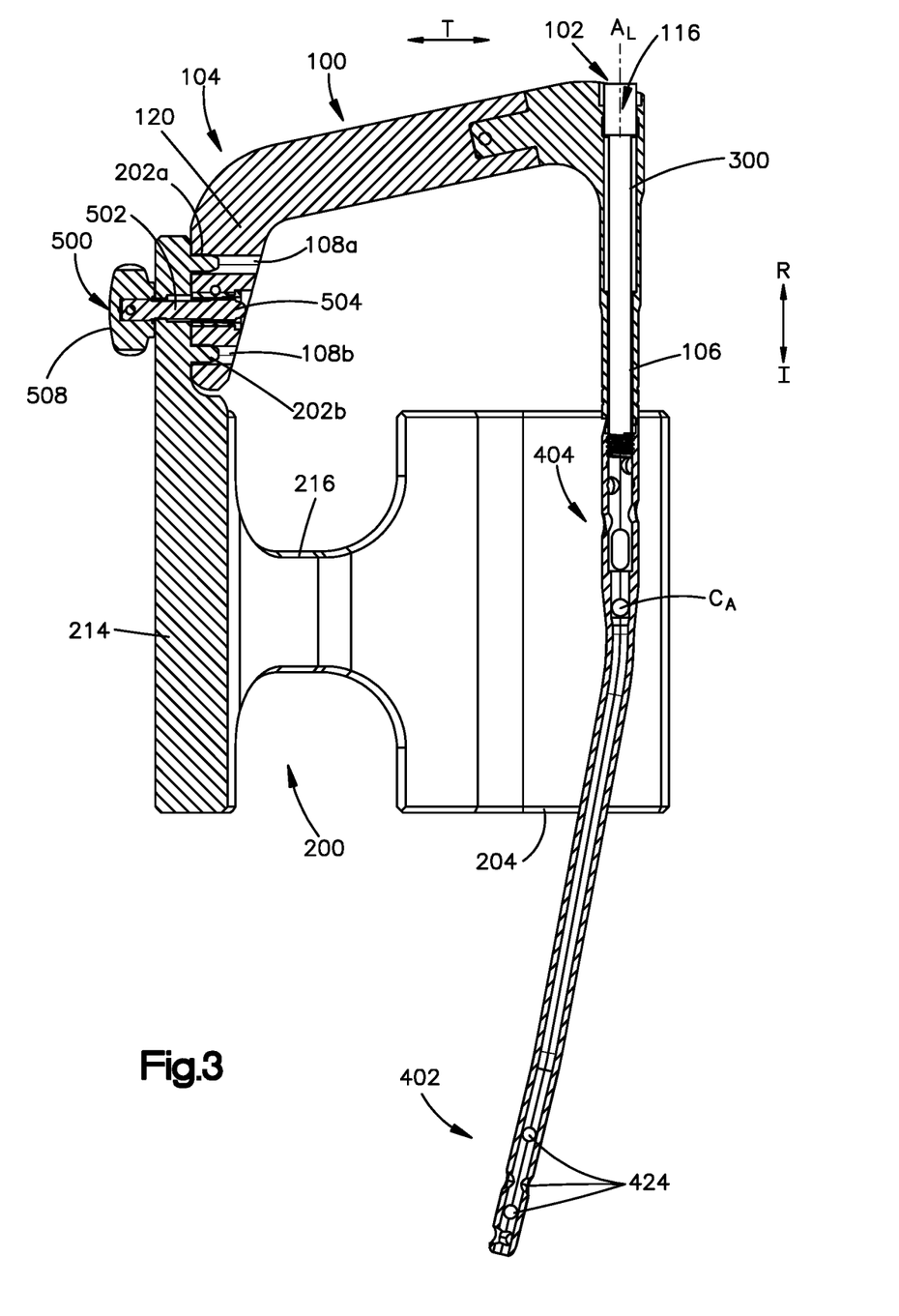
FIG. 3 shows a cross-sectional view of the intramedullary nail insertion system of FIG. 1.

Referring now more specifically to the details of the system of FIGS. 1-3, the spacer 100 is configured to support the targeting guide 200 relative to the intramedullary nail 400 such that a surface of the at least one solid portion 205 of the guide body 204 of the targeting guide 200 is spaced radially outward from the intramedullary nail 400. The spacer 100 has a first transverse end 102 and a second transverse end 104 that are offset from one another along a select transverse direction T. The select transverse direction T can be a radial direction that extends radially out relative to an axis of the intramedullary nail 400 when the spacer 100 is coupled to the intramedullary nail 400. The spacer 100 can have a trailing end 103, and a leading end 105 that is offset from the trailing end 103 along an insertion direction I.

The first transverse end 102 of the spacer 100 comprises a coupler 106 that is configured to couple to the intramedullary nail 400. The coupler 106 can be configured to couple to the intramedullary nail 400 so as to fix a rotational orientation of the coupler 106 relative to the intramedullary nail 400 about a central axis $A_L$. In some embodiments, the coupler 106 have a cylindrical shape that extends along the insertion direction I. The central axis $A_L$ can be a central axis of at least one of the coupler 106 and a trailing end 404 of the intramedullary nail 400. The coupler 106 can define at least one mating feature, such as at least one of a protrusion 107 and a recess 109, that is configured to engage a corresponding at least one mating feature of the intramedullary nail 400, such as at least one of a recess 416 and a protrusion 414 (shown in FIG. 6 and discussed below), so as to fix a rotation orientation of the coupler 106 relative to the intramedullary nail 400. The coupler 106, and hence the at least one mating feature, can be disposed at the leading end 105 of the spacer 100. In some embodiments, the coupler 106 can include a plurality of protrusions 107 (labeled in the enlarged view of FIG. 2), each configured to engage a corresponding recess 416 of the intramedullary nail 400. In such embodiments, each adjacent ones of the protrusions 107 can be separated a recess 109.

When the spacer 100 is coupled to the intramedullary nail 400, the at least one mating feature of the spacer 100 engages the at least one mating feature of the intramedullary nail 400 so as to prevent the intramedullary nail 400 from rotating relative to the spacer 100. Moreover, in some embodiments, the at least one mating feature of the coupler 106 can be configured such that the spacer 100 can be coupled to the intramedullary nail 400 in only one select rotational orientation. Thus, the at least one mating feature can be configured so as to prevent the spacer 100 from being coupled to the intramedullary nail 400 in any other rotational orientation other than the select rotational orientation. This can ensure that the central axis $C_A$ of each of the at least one bone-anchor fixation hole 422 properly aligns with (i) the same point on the surface of the at least one solid portion 205 of the guide body 204 of the targeting guide 200 in the event that the targeting guide 200 and intramedullary nail 400 are decoupled from, and then recoupled, to one another before formation of the at least one alignment aperture 218, or (ii) a respective one of the at least one alignment aperture 218, in the event that the targeting guide 200 is decoupled from, and then recoupled to, the intramedullary nail 400 after formation of the at least one alignment aperture 218.

The spacer 100 can define a cannulation 116 (labeled in FIG. 3) that extends through the first transverse end 102, such as through the coupler 106, along the insertion direction I. The spacer 100 can be configured (e.g., sized and shaped) such that the cannulation 116 aligns with a cannulation 426 of the intramedullary nail 400 when the spacer 100 is coupled to the intramedullary nail 400. The cannulation 116 can be configured (e.g., sized and shaped) so as to receive a rod, such as a guide rod or reaming rod, therethrough. In some embodiments, the spacer 100 can be implemented as an insertion handle, and the handle can be used to guide the intramedullary nail 400 along the guide rod or reaming rod into the medullary canal of the bone during insertion of the intramedullary nail 400. The cannulation 116 can extend through the coupler 106.

The second transverse end 104 of the spacer 100 can comprise a coupler 120 that is configured to couple the spacer 100 to the targeting guide 200, although, in alternative embodiments, the spacer 100 and targeting guide can be monolithic with one another. The coupler 120 can be configured to couple the spacer 100 to the targeting guide 200 so that the spacer 100 and targeting guide 200 are positionally fixed relative to one another. Thus, when coupled to the targeting guide 200, the spacer 100 can be fixed (e.g., translationally and rotationally) to the targeting guide 200.

In some embodiments, the spacer 100 can be an insertion handle. For example, the spacer 100 can have an outer surface 114 between the first end 102 and the second end 104. The outer surface 114 can define a grip that is configured to be grasped by a hand of a medical professional during insertion of the intramedullary nail 400. Thus, the spacer 100 can be grasped by a medical professional to guide the intramedullary nail 400 into the medullary canal. It will be understood, however, that the spacer 100 need not be an insertion handle, and that a separate insertion handle can be coupled to the intramedullary nail 400 to implant the intramedullary nail 400 before targeting the at least one bone-anchor fixation hole 422 with the targeting guide 200. In other embodiments, the spacer 100 may be larger than may be effectively gripped by a user. The spacer 100 may be straight between the first transverse end 102 and second transverse end 104, or may have one or more curves or bends (not shown) between the first transverse end 102 and second transverse end 104. The spacer 100 may be formed of a single unitary piece of material or may be formed from multiple components that are coupled to one another.

In one embodiment, the system can comprise a fastener 300 (shown in FIGS. 2 and 3) that is configured to fasten the spacer 100 to the intramedullary nail 400 so as to positionally fix the spacer 100 and intramedullary nail 400 to one another. The fastener 300 can be configured as any suitable fastener, and various such fasteners are known in the art. FIG. 2 shows one example fastener 300 that has a first coupler end 302, and a second end 304 offset from the first coupler end 302 along the insertion direction I. The second coupler end 304 can include threading 308 that is configured to engage threading 410 (see FIG. 6) of the intramedullary nail 400 so as to secure the fastener 300 to the intramedullary nail 400, although it will be understood that the second coupler end 304 can include a quick connect/disconnect or other suitable feature other than threading. In one embodiment, the threading 308 can be male threading that is configured to engage female threading of the intramedullary nail 400.

The first coupler end 302 can include an engagement surface 306 that is configured to be engaged by an instrument or a medical professional so as to rotate the fastener 300 to engage the threading 308 of the fastener 300 with the threading 410 of the intramedullary nail 400. In one embodiment, the engagement surface 306 can be an internal surface that defines a non-circular cross-section, such as a hexagon, polygon, or other shape, that can be engaged by a driving instrument such that rotation of the driving instrument causes a corresponding rotation of the fastener 300. In other embodiments, the engagement surface 306 can be a handgrip that can be gripped by a user's hand to secure the fastener 300 to the intramedullary nail 400.

The fastener 300 can include a stop or a shoulder 310 that is configured to abut the spacer 100 when the fastener 300 is secured to the intramedullary nail 400 so as to prevent the spacer 100 from moving in a rearward direction R, opposite the insertion direction I, relative to the intramedullary nail 400. The stop or shoulder 310 has a cross-sectional dimension in a plane that is perpendicular to the insertion direction I. The cross-sectional dimension can be measured from a first point on the stop or shoulder to a second point on the stop or shoulder, the first and second points being on opposed sides of the axis $A_L$. Further, the cross-sectional dimension of the stop or shoulder 310 can be greater than a cross-sectional dimension of the cannulation 116 such that the spacer 100 limits an insertion depth of the stop or shoulder 310 into the cannulation 116 along the insertion direction I. Thus, when the spacer 100 is coupled to the intramedullary nail 400, the spacer 100 can be trapped between the intramedullary nail 400 and the stop or shoulder 310 of the fastener 300.

With continued reference to FIGS. 1-3, the targeting guide 200 has a first guide end 201, and a second guide end 203 opposite the first guide end 201 along the insertion direction I. The targeting guide 200 has a guide body 204 that extends between the first guide end 201 and the second guide end 203. The targeting guide 200 can comprise a coupler 202 that is configured to couple the targeting guide 200 to the spacer 100 at an attachment location, although, in alternative embodiments, the spacer 100 and targeting guide 200 can be monolithic with one another at the attachment location. The coupler 202 can be attached to the guide body 204. For example, the guide body 204 can extend from the coupler 202, such as along the insertion direction I. The coupler 202 can be configured to couple the targeting guide 200 to the spacer 100 so that the spacer 100 and targeting guide 200 are positionally fixed relative to one another. Thus, when coupled to the spacer 100, the targeting guide 200 can be fixed to the spacer 100 with respect to translation and rotation.

The guide body 204 has an inner guide surface 210, and an outer guide surface 212 that is opposite the inner surface 210. The inner guide surface 210 can be positioned closer to the intramedullary nail 400 than the outer guide surface 212 when the targeting guide 200 is coupled to the intramedullary nail 400. The guide body 204 has at least one solid portion 205 that is devoid of any through-holes. The at least one solid portion 205 can include at least a portion of the inner guide surface 210. The at least one solid portion 205 can extend between the inner guide surface 210 and the outer guide surface 212, such as from the inner guide surface 210 to the outer guide surface 212. The at least one solid portion 205 is preferably solid from the inner guide surface 210 to the outer guide surface 212. However, in alternative embodiments, the guide body 204 can have a cavity (not shown) between the inner surface 210 and the outer surface 212 at the at least one solid portion 205. The at least one solid portion 205 can include at least a portion, up to an entirety, of the inner guide surface 210. At least a portion of the guide body 204, such as a portion or portions that include the at least one solid portion 205, can be formed from a material, such as a polymer, that is radiolucent and that can be easily drilled. At least a portion of the guide body 204, such as a portion or portions that include the at least one solid portion 205, can be molded, such as injection molded. The targeting guide 200 is preferably formed from a material or materials that are sufficiently rigid so as to prevent the targeting guide 200 from deflecting when the at least one alignment aperture 218 is formed therein.

At least one solid portion 205 of the guide body 204 (e.g., at 214) can be aligned along the insertion direction I with an attachment location of the targeting guide 200 that attaches to the spacer 100. For example, in embodiments where the spacer 100 and targeting guide 200 are separate components, as opposed to being monolithic with one another, at least one solid portion 205 can be aligned with the coupler 202 along the insertion direction I. In addition, or alternatively, at least a portion of the guide body 204 can extend circumferentially about the intramedullary nail 100 when the targeting guide 200 is coupled to the intramedullary nail 100. Note that the targeting guide 200 can have any suitable shape so as to align the at least one solid portion 205 of the inner surface 210 with a central axis $A_c$ of at least one of the bone-anchor fixation holes 422.

The coupler 202 of the targeting guide 200 can define at least one mating feature that is configured to mate with at least one mating feature of the coupler 120 of the spacer 100. For example, the at least one mating feature of the targeting guide 200 can include at least one of a protrusion and a recess, and the at least one mating feature of the spacer 100 can include another one of the at least one of the protrusion and recess. The at least one of the protrusion and recess of the targeting guide 200 can be configured to mate with the at least one of the protrusion and a recess of the spacer 100. In one example, the targeting guide 200 can include at least two mating features, such as a pair of protrusions 202a and 202b, that are configured to mate with at least two mating features of the spacer 100, such as a pair of recesses 108a and 108b. The at least two mating features of each of the targeting guide 200 and the spacer 100 can be offset from one another. The mating features of the targeting guide 200 and spacer 100 can be configured such that, when mated, the mating features limit rotation of the targeting guide relative to the spacer 100 about an axis $C_F$ (see FIG. 2) that extends along the transverse direction T.

The intramedullary nail insertion system can include a fastener 500 that that is configured to secure the targeting guide 200 to the spacer 100, although the fastener 500 can be omitted in embodiments where the targeting guide 200 and spacer 100 are integral to one another. The fastener 500 can be configured to secure the targeting guide 200 to the spacer 100 so as to limit or prevent translation of the targeting guide 200 relative to the spacer along the transverse direction T.

In one example, the fastener 500 can include a shaft 502 having a first end 504 and a second end 506. The first end 504 can be configured to attach to at least one of the spacer 100 and the targeting guide 200. For example, the first end 504 can include threading that is configured to engage threading of at least one of the spacer 100 and the targeting guide 200, although fastening mechanisms other than threading are contemplated. The second end 506 of the fastener 500 can include a drive surface 508 that is configured to be engaged by a user or instrument to turn the fastener 500. In one example, the drive surface 508 can define a handle, although the drive surface 508 could alternatively include a socket that is configured to receive a drive surface of a driving instrument such as a screw driver. The fastener 500 can include an inner surface 510 that has a cross-sectional dimension that is greater than a cross-sectional dimension of the shaft 502. The inner surface 510 can be part of the handle, although embodiments of the disclosure are not so limited.

The coupler 120 of the spacer 100 can have an opening 122, and the coupler 202 of the targeting guide 200 can have an opening 208 that is configured to be aligned with the opening 122 along an axis AF when the spacer 100 and targeting guide 200 are coupled to one another. The shaft 502 of the fastener 500 can be configured to be received through the opening of one of the spacer 100 and the targeting guide 200 into the opening of another one of the spacer 100 and the targeting guide 200. At least one of the opening 122 and opening 208 can define threading that is configured to receive the threading of the fastener 500 (in embodiments that employ threading). When the second end 506 of the shaft 502 is fastened to one of the spacer 100 and the targeting guide 200, the other of the spacer 100 and the targeting guide 200 can be trapped between the inner surface 510 of the fastener 500 and the one of the spacer 100 and the targeting guide 200 so to prevent translation of the spacer 100 and targeting guide 200 relative to one another along the transverse direction T.

Figures 6, 7:
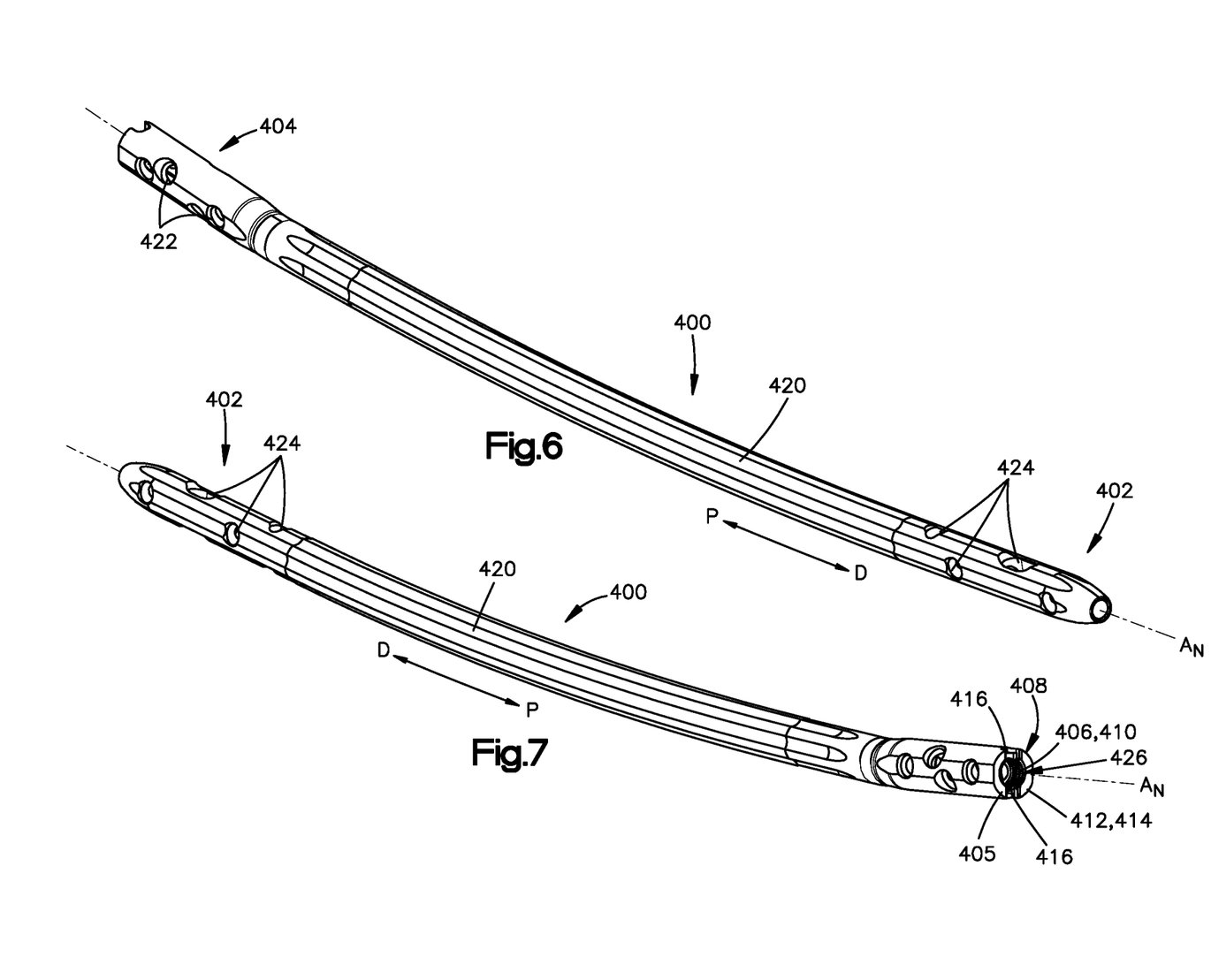
FIG. 6 shows a first perspective view of an intramedullary nail of the intramedullary nail system of FIG. 1 according to one embodiment.
FIG. 7 shows a second perspective view of the intramedullary nail of FIG. 6.

Referring now to FIGS. 6 and 7, an intramedullary nail 400 is shown according to one embodiment. It will be understood that intramedullary nail 400 is but one example, and that other intramedullary nails can be used with the system described herein. The intramedullary nail 400 has an insertion or leading end 402, and a trailing end 404 offset from the leading end 402 along the rearward direction R, opposite the insertion direction I. The leading and trailing ends 402 and 404 can be spaced from one another along a central nail axis $A_N$ that can be straight or bent. Further, the intramedullary nail 400 has an outer surface 420 that extends between the leading and trailing ends 402 and 404, such as from the leading end 402 to the trailing end 404. In some embodiments, the intramedullary nail 400 can define a cannulation 426 that extends therein between the leading and trailing ends 402 and 404. The trailing end 404 can include a fastener 406 that is configured to receive the fastener 300. For example, the fastener 406 can define a recess or opening 408 that is configured to receive the fastener end 304. The fastener 406 can include female threading 410 that engages male threading of the fastener 300, although other fastening mechanisms are contemplated.

The trailing end 404 can also include a fastener 412 that is configured to engage the coupler 106 of the spacer 100 so as to rotatably fix the spacer 100 and intramedullary nail 400 relative to one another with respect to rotation about the central nail axis $A_N$. In one embodiment, the fastener 412 can comprise at least one of a protrusion 414 and a recess 416 that is configured to engage a corresponding one of a recess and a protrusion of the spacer 100. For example, the fastener 412 can comprise at least one protrusion 414, such a plurality of protrusions or teeth. Each protrusion 414 can be configured to engage at least one corresponding recess in the spacer 100. Each of the at least one protrusion 414 can extend from a trailing end surface 405 of the intramedullary nail 400 towards the leading end 402 of the nail 400. The fastener 414 can define at least one recess 416, such as a plurality of recesses, that extends into the trailing end surface 405 towards the leading end 402. Each of the at least one recess 416 can be configured to receive a corresponding protrusion 107 of the spacer 100. Further, in embodiments having a plurality of protrusions 414, each of the at least one recess 416 can extend between adjacent ones of the protrusions 414. Thus, in such embodiments, the protrusions 414 and recesses 416 can alternate around the opening 408.

The intramedullary nail further defines a set of one or more trailing bone-anchor fixation holes 422 that extend through the outer surface 420 at the trailing end 404, and a set of one or more leading bone-anchor fixation holes 424 that extend through the outer surface 420 at the leading end 402. The set of one or more trailing holes 422 are configured to be disposed on a first side of a fracture in a bone that defines the medullary canal, and the set of one or more leading holes 424 are configured to be disposed on a second side of the fracture in the bone. Thus, the nail 400 can be configured such that the fracture is to be disposed between the set of one or more trailing holes 422 and the set of one or more leading holes 424. Each trailing aperture 422 and each leading aperture 424 is configured to receive a bone anchor such that the bone anchor fixedly attaches the intramedullary nail 400 to the bone. Each bone-anchor fixation hole 422 and 424 can be either locking aperture having threads that are configured to be engaged by threads of bone screws, or can be non-locking apertures.

Figure 8:
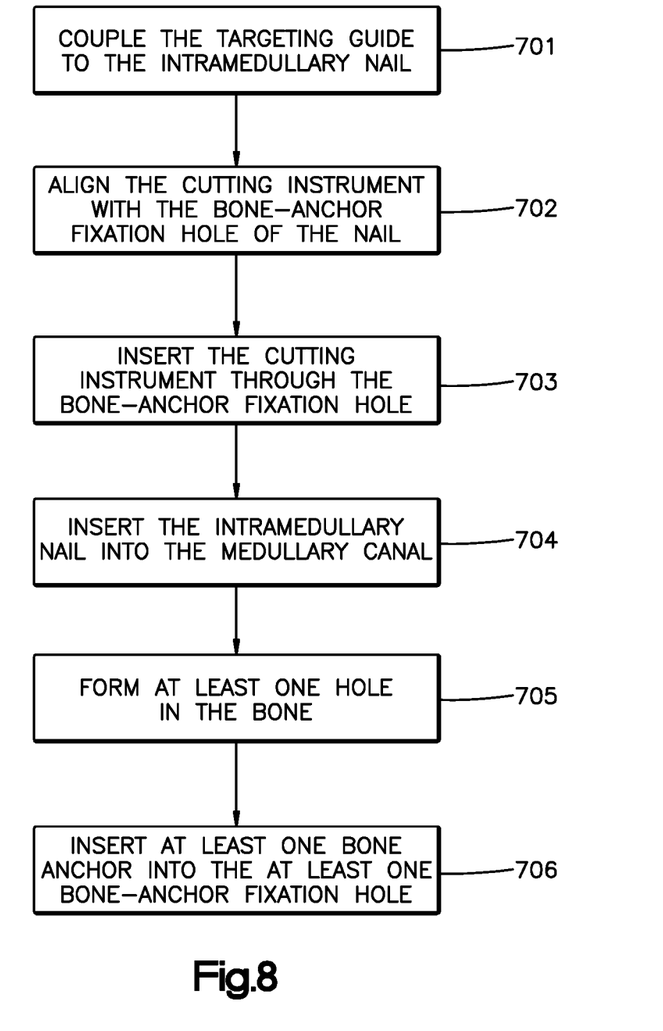
FIG. 8 shows a simplified flow diagram of a method of using an intramedullary nail insertion system according to one embodiment.

Turning now to FIG. 8, a method of using the intramedullary insertion system will be described. The method comprises a step 701 of coupling the targeting guide 200 to the intramedullary nail 400. In one example, where the spacer 100 and targeting guide 200 are separable components, the coupling step 701 can comprise a step of coupling the targeting guide 200 to the spacer 100 and a step of coupling the spacer 100 to the intramedullary nail 400. The targeting guide 200 can be coupled to the spacer 100 before or after the spacer 100 is coupled to the intramedullary nail 400. In another example, where the spacer 100 and targeting guide 200 are monolithic with one another, the coupling step 701 can comprise a step of coupling the spacer 100 to the intramedullary nail 400, without separately coupling the spacer 100 to the targeting guide 200. Note that, in some embodiments, the targeting guide 200 can be pre-coupled to the spacer 100 such that the step of coupling the targeting guide 200 to the spacer 100 can be omitted. Additionally, or alternatively, the spacer 100 can be pre-coupled to the intramedullary nail 400 such that the step of coupling the spacer 100 to the intramedullary nail 400 can be omitted. When the targeting guide 200 is coupled to the intramedullary nail 400, the central axis $C_A$ of at least one bone-anchor fixation hole 422 intersects a surface of at least one solid portion 205 of the targeting guide 200.

The method can comprise a step 702 of aligning an axis of a cutting instrument 600, such as a drill bit or reamer, with a bone-anchor fixation hole 422 of the intramedullary nail 400. The cutting instrument 600 can be aligned on a side of the intramedullary nail 400 that is opposite the at least one solid portion 205 of the inner surface 210 of the targeting guide 200.

The method can comprise a step 703 of inserting the cutting instrument 600 through the bone-anchor fixation hole 422 such that the cutting instrument 600 is in contact with the inner surface 210 of the targeting guide 200, where the targeting guide 200 is supported relative to the intramedullary nail 400 such that the inner surface 210 is spaced outwardly from the outer surface 420 of the intramedullary nail 400 along a radial direction.

The method can comprise a step 704 of driving the cutting instrument 600 through the guide body 204 of the targeting guide 200 so as to form an alignment aperture 218 in the targeting guide 200. The alignment aperture 218 should have a central axis $C_A$ that is aligned with the bone-anchor fixation hole 422. Note that, in performing steps 703 and 704, a guide sleeve (not shown) can be coupled to the bone-anchor fixation hole 422 such that the guide sleeve extends from the intramedullary nail 400 towards the inner surface 210 of the targeting guide 200. The guide sleeve can then provide additional guidance as the cutting instrument 600 is inserted through the guide sleeve and into the targeting guide 200 to form the alignment aperture 218. Steps 702 and 703 can be repeated one or more times to form one or more additional alignment apertures 218. Steps 702 and 703 (and optionally step 701) can be performed within a surgical facility such as at a back table of the surgical facility. Alternatively, steps 701 to 703 can be performed prior to shipping the intramedullary nail insertion system to the surgical facility, such as in a manufacturing facility. In some embodiments, the method can comprise a step of enlarging the alignment aperture 218 using a larger cutting instrument, such as a larger drill bit or reamer.

The method can comprise a step 704 of inserting the intramedullary nail 400 into the medullary canal of the bone. In one example, the inserting step 704 can comprise de-coupling the targeting guide 200 from the intramedullary nail 400, inserting the intramedullary nail 400 into the medullary canal, and then re-coupling the targeting guide to the intramedullary nail 400 such that the central axis $C_A$ of each of the at least one alignment apertures 218 is aligned with a corresponding bone-anchor fixation hole 422. In another example, the inserting step 704 can comprise inserting the intramedullary nail 400 into the medullary canal, while the targeting guide 200 remains coupled to the intramedullary nail 400. The intramedullary nail 400 is inserted into the medullary canal of a patient along the insertion direction I by applying a force to the nail 400 along the insertion direction. This may be achieved by, for example, using a hammer to drive the intramedullary nail 400 into the canal.

The method can comprise a step 705 of forming at least one hole in the bone that is aligned with the at least one bone-anchor fixation hole 422 of the intramedullary nail 400. The forming step 705 can comprise a step of aligning a central axis of a cutting instrument, such as a drill bit or reamer, with the at least one alignment aperture 218 of the targeting guide 200, a step of inserting the cutting instrument through the at least one alignment aperture 218 such that the cutting instrument is in contact with the bone, and a step of driving the cutting instrument through the bone to the at least one bone-anchor fixation hole 422 of the intramedullary nail 400. In one example, step 705 can comprise attaching at least one sleeve to the at least one alignment aperture 218 of the targeting guide 200 such that the at least one sleeve extends from the at least one alignment aperture 218 towards the bone. The cutting instrument can be inserted through the at least one sleeve such that the sleeve protects the surrounding soft tissue as the cutting instrument cuts into the bone.

The method can comprise a step 706 of inserting at least one bone anchor through the bone and into the at least one bone-anchor fixation hole 422. The step 706 can comprise inserting the at least one bone anchor through the at least one alignment aperture 218. In one example, the at least one bone anchor can be inserted through the at least one sleeve such that the sleeve protects the surrounding soft tissue as the bone anchor is passed therethrough. In one such example, the at least one sleeve can comprise a first sleeve, and a second sleeve disposed within the first sleeve. The second sleeve can be sized to receive the cutting instrument, and the first sleeve can be sized to receive the at least one bone anchor after the first sleeve has been removed after cutting the hole in the bone. Steps 705 and 706 can be repeated for each additional bone anchor to be inserted into a bone-anchor fixation hole 422 of the intramedullary nail 400.

In step 704, the intramedullary nail 400 can be implanted by driving the nail 400 into a medullary canal of a long bone such as a tibia, fibula, humerus, or femur. Prior to insertion of the assembly 400, a medical professional can enlarge the medullary canal to make room for the nail 400. For example, the medullary canal can be enlarged by inserting a reaming rod (not shown) down the medullary canal, and guiding a reamer head (not shown) with at least one cutting edge down the reaming rod such that the at least one cutting edge bores out the medullary canal. The reaming rod can be flexible so as to bend with the contour of the medullary canal. In some examples, the distal end of the reaming rod can have an enlarged distal tip, such as a ball-shaped tip, that can prevent the reamer head from traveling past the distal end of the reaming rod. After enlarging the medullary canal, the intramedullary nail 400 is driven down into the enlarged medullary canal. In some cases, the reamer head can be removed, leaving the reaming rod in place, and the intramedullary nail assembly 100 can then be guided down the reaming rod into the medullary canal. As such, the reaming rod can be received in the cannulation 426 of the intramedullary nail 400 as the nail 400 is driven down the reaming rod into the medullary canal.

Typically, the reamer head should be selected based on the size of the intramedullary nail 400. However, medical professionals can have difficulty in selecting an appropriately sized reaming rod for a particular intramedullary nail and reamer head. On the one hand, if a reaming rod is selected in which the distal tip is too small, then the reaming head can translate past the distal tip, thereby cutting further into the bone than needed. On the other hand, if a reaming rod is selected in which the distal tip is larger than the cannulation 426 of the nail 400, then the distal tip might not fit through the cannulation 426 of the intramedullary nail 400. In such a case, it may be difficult, or impossible, to pull the distal tip through the cannulation 426 so as to remove the reaming rod from the intramedullary nail 400 after the nail 400 is implanted.

In one aspect of the disclosure, one or more, up to all, of the spacer 100, the targeting guide 200, the fastener 300, and the intramedullary nail 400 can include a verification hole (not shown) that is configured to receive at least a portion of the reaming rod, such as the distal tip. The verification hole, which can also be referred to as a go/no-go hole, can have a cross-sectional dimension that is specific to the size of the specific intramedullary nail 400 that is being used. In particular, the verification hole can have a cross-sectional dimension that corresponds to a size of an appropriately-sized reaming rod, such as to a cross-sectional dimension of the distal tip. Before inserting the reaming rod into the medullary canal, the medical professional can insert the distal tip of the reaming rod into the verification hole to determine whether the reaming rod is an appropriate size. The medical professional can repeat this step until an appropriately-sized reaming rod is identified. The appropriately-sized reaming rod can then be used to implant the intramedullary nail 400.

Referring briefly to FIG. 5, the targeting guide 200 of FIGS. 1 to 3 is shown according to one embodiment with an alignment aperture 218 formed therein. Although not shown, the targeting guide 200 can have one or more additional alignment apertures 218 formed therein. The targeting guide 200 is manufactured in accordance with steps 702 to 704 (and optionally step 701). Each alignment aperture 218 has a central axis $C_A$ that is aligned with a bone-anchor fixation hole 422 when the targeting guide 200 is coupled to the intramedullary nail 400. The central axis $C_A$ of each alignment aperture 218 can extend along the same direction as a central axis of a respective one of the bone-anchor fixation holes 422. In at least some embodiments, the central axis $C_A$ of each alignment aperture 218 can be in-line or co-linear with a central axis of a corresponding bone-anchor fixation hole 422.

According to various embodiments, targeting guides of the disclosure may be formed from relatively inexpensive materials, such as polymers, including thermoplastics. The use of inexpensive materials may reduce manufacture costs compared to conventional alignment guides that are not custom constructed to a specific nail and that are formed from more expensive materials. Using less expensive materials may also make it more practical to dispose each targeting guide after a single use. This can also eliminate a need to sterilize the targeting guides between uses.

In addition, each pre-customized targeting guide of the disclosure can be used with a wider range of intramedullary nails than a comparable conventional alignment guide. A comparable conventional alignment guide is typically constructed to be usable only with an intramedullary nail having a specific size, shape, and bone-anchor fixation hole pattern. A pre-customized targeting guide of the present disclosure, on the other hand, can be usable with a variety of different intramedullary nails having different sizes, shapes, and bone-anchor fixation hole patterns. In particular, a pre-customized targeting guide of the present disclosure can be customized by forming at least one alignment aperture 218 to match the bone-anchor fixation hole pattern of any intramedullary nail in a variety of differently sized and shaped intramedullary nails.

Although there has been shown and described the certain embodiments of the present disclosure, it will be readily apparent to those skilled in the art that modifications may be made thereto which do not exceed the scope of the appended claims. The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The invention claimed is:

1. An intramedullary nail insertion system, comprising:
   a targeting guide having a guide body that has at least one solid portion;
   a spacer configured to couple the targeting guide to an intramedullary nail that defines a bone-anchor fixation hole that extends along a central axis, wherein the spacer and targeting guide are configured such that, when the spacer couples the targeting guide to the intramedullary nail, the guide body of the targeting guide is spaced radially outward from the intramedullary nail and a solid surface of the at least one solid portion is intersected by an entirety of the bone-anchor fixation hole of the intramedullary nail, such that a drill bit driven through the bone-anchor fixation hole is configured to create an alignment hole that extends through the at least one solid portion to create an alignment hole that is aligned with the bone-anchor fixation hole.

2. The intramedullary nail insertion system of claim 1, comprising the intramedullary nail, wherein the intramedullary nail has a trailing end, a leading end that is offset from the trailing end, and an outer surface that extends between the trailing end and the leading end, and wherein the intramedullary nail defines the at least one bone-anchor fixation hole that extends through the outer surface.

3. The intramedullary nail insertion system of claim 1, wherein the at least one solid portion of the targeting guide is formed from a polymer.

4. The intramedullary nail insertion system of claim 1, wherein the targeting guide is configured such that at least a portion of the guide body extends circumferentially about the intramedullary nail when the targeting guide is coupled to the intramedullary nail.

5. The intramedullary nail insertion system of claim 1, wherein the targeting guide comprises a coupler that is configured to couple the guide body to the spacer.

6. The intramedullary nail insertion system of claim 1, wherein the spacer defines a handle.

7. The intramedullary nail insertion system of claim 1, wherein the spacer comprises a coupler that is configured to couple to a trailing end of the intramedullary nail.

8. The intramedullary nail insertion system of claim 1, wherein the spacer and targeting guide are monolithic with one another.

9. The intramedullary nail insertion system of claim 1, wherein the spacer and targeting guide are configured to couple to one another.

* * * * *